United States Patent [19]

Klotz

[11] Patent Number: 4,584,415
[45] Date of Patent: Apr. 22, 1986

[54] FORMATION OF ALKYL ETHERS FROM ALCOHOLS AND ALKENES USING AMS-1B CRYSTALLINE BOROSILICATE

[75] Inventor: Marvin R. Klotz, Batavia, Ill.
[73] Assignee: Standard Oil Company (Indiana), Chicago, Ill.
[21] Appl. No.: 742,989
[22] Filed: Jun. 10, 1985

Related U.S. Application Data

[63] Continuation of Ser. No. 427,011, Sep. 29, 1982.

[51] Int. Cl.$^4$ ............................................. C07C 41/06
[52] U.S. Cl. .................................................... 568/697
[58] Field of Search ........................................ 568/697

[56] References Cited

U.S. PATENT DOCUMENTS

| | | | |
|---|---|---|---|
| 3,966,586 | 6/1976 | Owen et al. ........................... | 568/697 |
| 4,268,420 | 5/1981 | Klotz .................................... | 585/408 |
| 4,269,813 | 5/1981 | Klotz .................................... | 423/326 |

FOREIGN PATENT DOCUMENTS

| | | | |
|---|---|---|---|
| 0055045 | 6/1982 | European Pat. Off. | |
| 1814488 | 7/1970 | Fed. Rep. of Germany ... | 252/455 Z |
| 133661 | 1/1977 | German Democratic Rep. .................................... | 568/697 |
| 46-27374 | 8/1971 | Japan .............................. | 252/455 Z |
| 103379 | 8/1979 | Poland ............................... | 568/697 |

*Primary Examiner*—Natalie Trousof
*Assistant Examiner*—Bruce D. Gray
*Attorney, Agent, or Firm*—Wallace L. Oliver; William T. McClain; William H. Magidson

[57] ABSTRACT

A process to form an ether comprises contacting an alkene and an alcohol under conversion conditions with an AMS-1B borosilicate catalyst composition.

20 Claims, No Drawings

[4,584,415]

FORMATION OF ALKYL ETHERS FROM ALCOHOLS AND ALKENES USING AMS-1B CRYSTALLINE BOROSILICATE

This is a continuation, of application Ser. No. 427,011, filed Sept. 29, 1982.

BACKGROUND OF THE INVENTION

This invention relates to formation of ethers and more particularly relates to formation of alkyl ethers from alcohols and alkenes using an AMS-1B crystalline borosilicate-based catalyst.

Alkyl ethers are compounds with a general formula R—O—R' where R and R' are alkyl groups. Typically, ethers are neutral, comparatively unreactive compounds having low solubility in water but easily soluble in organic liquids and frequently used as solvents in organic synthesis, plasticizers, anesthetics and fumigants. Methyl t-butyl ether particularly is useful as an octane booster in gasoline.

Conventionally, ethers can be prepared by reaction of an alkyl halide and sodium alcoholate (Williamson synthesis), by dehydration of alcohols with strong acids and by addition of an alcohol to an olefin under acid catalysis such as by sulfuric acid, phosphoric acid, hydrochloric acid and boron trifluoride. Methyl t-butyl ether can be made from isobutylene and methanol in the presence of an acidic ion-exchange resin catalyst. Ethers, their preparation, properties and uses are described in Kirk-Othmer, *Encyclopedia of Chemical Technology*, Third Edition, Vol. 9, pp. 381-393, incorporated by reference herein.

Zeolitic materials, both natural and synthetic, are known to have catalytic capabilities for many hydrocarbon processes. Zeolitic materials typically are ordered porous crystalline aluminosilicates having a definite structure with cavities interconnected by channels. The cavities and channels throughout the crystalline material generally are uniform in size allowing selective separation of hydrocarbons. Consequently, these materials in many instances are known in the art as "molecular sieves" and are used, in addition to selective adsorptive processes, for certain catalytic properties. The catalytic properties of these materials are affected to some extent by the size of the molecules which selectively penetrate the crystal structure, presumably to contact active catalytic sites within the ordered structure of these materials.

Generally, the term "molecular sieve" includes a wide variety of both natural and synthetic positive-ion-containing crystalline zeolite materials. They generally are characterized as crystalline aluminosilicates which comprise networks of $SiO_4$ and $AlO_4$ tetrahedra in which silicon and aluminum atoms are cross-linked by sharing of oxygen atoms. The negative framework charge resulting from substitution of an aluminum atom for a silicon atom is balanced by positive ions, for example, alkali-metal or alka- line-earth-metal cations, ammonium ions, or hydrogen ions.

Prior art developments have resulted in formation of many synthetic zeolitic crystalline materials. Crystalline aluminosilicates are the most prevalent and, as described in the patent literature and in the published journals, are designated by letters or other convenient symbols. Examples of these materials are Zeolite A (U.S. Pat. No. 2,882,243), Zeolite X (U.S. Pat. No. 2,882,244), Zeolite Y (U.S. Pat. No. 3,130,007), Zeolite ZSM-4 (U.S. Pat. No. 3,578,723), Zeolite ZSM-5 (U.S. Pat. No. 3,702,886), Zeolite ZSM-11 (U.S. Pat. No. 3,709,979), Zeolite ZSM-12 (U.S. Pat. 3,832,449), Zeolite NU-1 (U.S. Pat. No. 4,060,590) and others.

Boron is not considered a replacement for aluminum or silicon in a zeolitic composition. However, recently a new crystalline borosilicate molecular sieve AMS-1B with distinctive properties was disclosed in U.S. Pat. Nos. 4,268,420 and 4,269,813 incorporated by reference herein. According to these patents AMS-1B can be synthesized by crystallizing a source of an oxide of silicon, an oxide of boron, an oxide of sodium and an organic template compound such as a tetra-n-propylammonium salt. The process of this invention uses AMS-1B crystalline borosilicate molecular sieve.

Hydrocarbon conversion processes are known using other zeolitic materials. Examples of such processes are dewaxing of oil stock (U.S. Pat. Nos. 3,852,189, 4,221,635 and Re. 28,398); conversion of lower olefins (U.S. Pat. Nos. 3,965,205 and 3,960,978 and European patent application Ser. No. 31,675); aromatization of olefins and aliphatics (U.S. Pat. Nos. 3,761,389, 3,813,330, 3,827,867, 3,827,868, 3,843,740, 3,843,741 and 3,914,171); hydrocracking and oligomerization of hydrocarbons (U.S. Pat. Nos. 3,753,891, 3,767,568, 3,770,614 and 4,032,432); conversion of ethane to aromatics and $C_{3+}$ hydrocarbons (U.S. Pat. No. 4,100,218); conversion of straight-chain and slightly branched-chain hydrocarbons to olefins (U.S. Pat. No. 4,309,275 and 4,309,276); and conversion of $C_4$ paraffins to aromatics (U.S. Pat. No. 4,291,182).

A method to manufacture ethers directly from an alkene and an alcohol would be desirable and a method that would form ethers from readily available feedstocks in one step without excessive losses to undesirable by-products would be especially desirable. A process that forms methyl t-butyl ether from methanol and isobutylene would be advantageous.

SUMMARY OF THE INVENTION

A process to form an ether comprises contacting an alkene and an alcohol under conversion conditions with an AMS-1B borosilicate catalyst composition.

BRIEF DESCRIPTION OF THE INVENTION

This invention is a method to form an ether from an alcohol and an alkene using an AMS-1B crystalline borosilicate-based catalyst system.

The alkene/alcohol reactants used in the process of this invention can be in the presence of other substances such as other hydrocarbon-based molecules. Thus, a feedstream used in the process of this invention comprising an aliphatic alkene also can contain other hydrocarbons such as alkanes, aromatics, hydrogen, and inert gases.

The ethers formed using the process of this invention have the formula R—O—R' wherein R and R' are alkyl groups containing one to about eight and two to about six carbon atoms respectively. The sum of the number of carbon atoms in R and R' typically is about four to about ten.

In the process of this invention, ethers are formed from an aliphatic alcohol and an alkene. Typical alcohols contain one to about eight carbon atoms, preferably one to about three carbon atoms, and include methanol, ethanol, n-propanol, isopropanol, n-butanol, sec-butanol, isobutyl alcohol, t-butyl alcohol, n-amyl alcohol, n-hexyl alcohol and n-octyl alcohol. Primary and secondary alcohols are preferred. The most preferable alcohol is methanol. Alkenes useful in this invention contain two to about six carbon atoms and preferably about three to about five carbon atoms. Typical alkenes include ethylene, propylene, 1-butene, 2-butene, isobutylene, 1-pentene, 2-pentene, 1-hexene, 2-hexene, 3-hexene, 3-methyl-1-pentene, 3-methyl-1-butene, 2-methyl-2-butene and 2-methyl-2-pentene.

The catalyst useful in this invention is based on the crystalline borosilicate molecular sieve, AMS-1B, described in U.S. Pat. Nos. 4,268,420 and 4,269,813, incorporated herein by reference.

The catalyst system which is useful in this invention comprises a borosilicate catalyst system based on a molecular sieve material identified as AMS-1B. Details as to the preparation of AMS-1B are described in U.S. Pat. No. 4,269,813. Such AMS-1B crystalline borosilicate generally can be characterized by the X-ray pattern listed in Table I and by the composition formula:

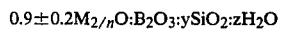

$$0.9\pm 0.2 M_{2/n}O:B_2O_3:ySiO_2:zH_2O$$

wherein M is at least one cation, n is the valence of the cation, y is between 4 and about 600 and z is between 0 and about 160.

TABLE I

| d-Spacing Å (1) | Assigned Strength (2) |
|---|---|
| 11.2 + 0.2 | W-VS |
| 10.0 ± 0.2 | W-MS |
| 5.97 ± 0.07 | W-M |
| 3.82 ± 0.05 | VS |
| 3.70 ± 0.05 | MS |
| 3.62 ± 0.05 | M-MS |
| 2.97 ± 0.02 | W-M |
| 1.99 ± 0.02 | VW-M |

(1) Copper K alpha radiation
(2) VW = very weak
W = weak
M = medium
MS = medium strong
VS = very strong The AMS-1B borosilicate molecular sieve useful in this invention can be prepared by crystallizing an aqueous mixture, at a controlled pH, of sources for cations, an oxide of boron, an oxide of silicon, and an organic template compound.

Typically, the mole ratios of the various reactants can be varied to produce the crystalline borosilicates of this invention. Specifically, the mole ratios of the initial reactant concentrations are indicated below:

|  | Broad | Preferred | Most Preferred |
|---|---|---|---|
| $SiO_2/B_2O_3$ | 5–400 | 10–150 | 10–80 |
| $R_2O^+/[R_2O^+ + M_{2/n}O]$ | 0.1–1.0 | 0.2–0.97 | 0.3–0.97 |
| $OH^-/SiO_2$ | 0.01 | 0.1–2 | 0.1–1 |
| $H_2O/OH^-$ | 10–4000 | 10–500 | 10–500 | wherein R is an organic compound and M is at least one cation having a valence n, such as an alkali-metal or an alkaline-earth-metal cation. By regulation of the quantity of boron (represented as $B_2O_3$) in the reaction mixture, it is possible to vary the $SiO_2/B_2O_3$ molar ratio in the final product.

More specifically, the material useful in the present invention is prepared by mixing a cation source compound, a boron oxide source, and an organic template compound in water (preferably distilled or deionized). The order of addition usually is not critical although a typical procedure is to dissolve sodium hydroxide and boric acid in water and then add the template compound. Generally, after adjusting the pH, the silicon oxide compound is added with intensive mixing such as that performed in a Waring Blender. After the pH is checked and adjusted, if necessary, the resulting slurry is transferred to a closed crystallization vessel for a suitable time. After crystallization, the resulting crystalline product can be filtered, washed with water, dried, and calcined.

During preparation, acidic conditions should be avoided. When alkali metal hydroxides are used, the values of the ratio of $OH^-/SiO_2$ shown above should furnish a pH of the system that broadly falls within the range of about 9 to about 13.5. Advantageously, the pH of the reaction system falls within the range of about 10.5 to about 11.5 and most preferably between about 10.8 and about 11.2.

Examples of oxides of silicon useful in this invention includes silicic acid, sodium silicate, tetraalkyl silicates and Ludox, a stabilized polymer of silicic acid manufactured by E. I. du Pont de Nemours & Co. Typically, the oxide of boron source is boric acid although equivalent species can be used such as sodium borate and other boron-containing compounds.

Cations useful in formation of AMS-1B include alkali-metal and alkaline-earth-metal cations such as sodium, potassium, lithium, calcium and magnesium. Ammonium cations may be used alone or in conjunction with such metal cations. Since basic conditions are required for crystallization of the molecular sieve of this invention, the source of such cation usually is a hydroxide such as sodium hydroxide. Alternatively, AMS-1B can be prepared directly in the hydrogen form by replacing such metal cation hydroxides with an organic base such as ethylenedi- amine.

Organic templates useful in preparing AMS-1B crystalline borosilicate include alkylammonium cations or precursors thereof such as tetraalkylammonium compounds. A useful organic template is tetra-n-propylammonium bromide. Diamines, such as hexamethylenediamine, can be used.

In a more detailed description of a typical preparation of this invention, suitable quantities of sodium hydroxide and boric acid ($H_3BO_3$) are dissolved in distilled or deionized water followed by addition of the organic template. The pH may be adjusted between about $11.0\pm 0.2$ using a compatible base or acid such as sodium bisulfate or sodium hydroxide. After sufficient quantities of silicic acid polymer (Ludox) are added with intensive mixing, preferably the pH is again checked and adjusted to a range of about $11.0\pm 0.2$. The resulting slurry is transferred to a closed crystallization vessel and reacted usually at a pressure at least the vapor pressure of water for a time sufficient to permit crystallization which usually is about 0.25 to about 20 days, typically is about one to about 10 days and preferably is about five to about seven days, at a temperature ranging from about 100° to about 250° C., preferably about 125° to about 200° C. The crystallizing material can be stirred or agitated as in a rocker bomb. Preferably, the crystallization temperature is maintained below the decomposition temperature of the organic template compound. Especially preferred conditions are crystallizing at about 165° C. for about five to about seven days. Samples of material can be removed during crystallization to check the degree of crystallization and determine the optimum crystallization time. The crystalline material formed can be separated and recovered by well-known means such as filtration with washing. This material can be mildly dried for anywhere from a few hours to a few days at varying temperatures, typically about 25°-200° C., to form a dry cake which can then be crushed to a powder or to small particles and extruded, pelletized, or made into forms suitable for its intended use. Typically, materials prepared after mild drying contain the organic template compound and water of hydration within the solid mass and a subsequent activation or calcination procedure is necessary, if it is desired to remove this material from the final product. Typically, mildly dried product is calcined at temperatures ranging from about 260° to about 850° C. and preferably about 525° to about 600° C. Extreme calcination temperatures or prolonged crystallization times may prove detrimental to the crystal structure or may totally destroy it. Generally there is no need to raise the calcination temperature beyond about 600° C. in order to remove organic material from the originally formed crystalline material. Typically, the molecular sieve material is dried in a forced draft oven at 165° C. for about 16 hours and is then calcined in air in a manner such that the temperature rise does not exceed 125° C. per hour until a temperature of about 540° C. is reached. Calcination at this temperature usually is continued for about 4 to 16 hours.

A catalytically active material can be placed onto the borosilicate structure by ion exchange, impregnation, a combination thereof, or other suitable contact means. Before placing a catalytically active metal ion or compound on the borosilicate structure, the borosilicate may be in the hydrogen form which, typically, is produced by exchange one or more times with ammonium ion, typically using ammonium acetate, followed by drying and calcination as described above.

The original cation in the AMS-1B crystalline borosilicate, which usually is sodium ion, can be replaced all or in part by ion exchange with other cations including other metal ions and their amine complexes, alkylammonium ions, ammonium ions, hydrogen ions, and mixtures thereof. Preferred replacing cations are those which render the crystalline borosilicate catalytically active, especially for hydrocarbon conversion. Typical catalytically active ions include hydrogen, metal ions of Groups IB, IIA, IIB, IIIA and VIII, and of manganese, vanadium, chromium, uranium, and rare earth elements.

Also, water soluble salts of catalytically active materials can be impregnated onto the crystalline borosilicate of this invention. Such catalytically active materials include metals of Groups IB, IIA, IIB, IIIA, IVB, VB, VIB, VIIB, and VIII, and rare earth elements.

Groups of elements referred to herein are those contained in the Periodic Table of Elements, *Handbook of Chemistry and Physics*, 54th Edition, CRC Press (1973).

Ion exchange and impregnation techniques are well-known in the art. Typically, an aqueous solution of a cationic species is exchanged one or more times at about 25° to about 100° C. A hydrocarbonsoluble metal compound such as a metal carbonyl also can be used to impregnate a catalytically active material. Impregnation of a catalytically active compound on the borosilicate or on a composition comprising the crystalline borosilicate suspended in and distributed throughout a matrix of a support material, such as a porous refractory inorganic oxide such as alumina, aften results in a suitable catalytic composition. A combination of ion exchange and impregnation can be used. Presence of sodium ion in a composition usually is detrimental to catalytic activity.

The amount of catalytically active material placed on the AMS-1B borosilicate can vary from about 0.01 weight percent to about thirty weight percent, typically from about 0.05 to about 25 weight percent, depending on the process use intended. The optimum amount can be determined easily by routine experimentation.

The AMS-1B crystalline borosilicate useful in this invention typically is admixed with or incorporated within various binders or matrix materials depending upon the intended process use. The crystalline borosilicate can be combined with active or inactive materials, synthetic or naturally-occurring zeolites, as well as inorganic or orqanic materials which would be useful for binding the borosilicate. Well-known materials include silica, silica-alumina, alumina, alumina sols, hydrated aluminas, clays such as bentonite or kaoline, or other binders wellknown in the art. Typically, the borosilicate is incorporated within a matrix material by blending with a sol of the matrix material and gelling the resulting mixture. Also, solid particles of the borosilicate and matrix material can be physically admixed. Typically, such borosilicate compositions can be pelletized or extruded into useful shapes. The crystalline borosilicate content can vary anywhere up to 100 wt. % of the total composition. Catalytic compositions can contain about 0.1 wt. % to about 75 wt. % crystalline borosilicate material and preferably contain about 5 wt. % to about 70 wt. % of such material.

Catalytic compositions comprising the crystalline borosilicate material of this invention and a suitable matrix material can be formed by adding a finelydivided crystalline borosilicate and a catalytically active metal compound to an aqueous sol or gel of the matrix material. The resulting mixture is thoroughly blended and gelled typically by adding a material such as ammonium hydroxide. The resulting gel can be dried and calcined to form a composition in which the crystalline borosilicate and catalytically active metal compound are distributed throughout the matrix material.

Specific details of catalyst preparations are described in U.S. Pat. No. 4,269,813.

In a process using this invention, a feedstream of an alkene and an alcohol is contacted with a catalytic material containing AMS-1B borosilicate-based catalyst. Generally, in the preferable process of this invention an alkene is contacted with the above-described AMS-1B borosilicate-based catalyst system in the liquid or vapor phase at a suitable reaction temperature, pressure and space velocity. Generally, suitable reaction conditions include a temperature of about 40° to about 200° C., a pressure of about 10 to about 100 atmospheres (1,000 to 10,000 kPa) or higher at a weight hourly space velocity (WHSV) of about 0.1 to about 24 $hr^{-1}$. In a typical process scheme, an alcohol and alkene-containing feedstream is contacted with such catalyst in a reactor at about 50° to about 150° C. at a pressure of about 12 to about 75 atmospheres (1,200 to 7,500 kPa) at a WHSV of about 0.5 to about 12 $hr^{-1}$. Preferably the ether formation process of this invention is conducted at about 60° to about 140° C. at a pressure of about 15 to about 60 atmospheres (150–600 kPa) at a WHSV of about 1.0 to about 10 $hr^{-1}$.

This invention is demonstrated but not limited by the following Example.

EXAMPLE I

A sample of AMS-1B crystalline borosilicate was prepared by dissolving 11,000 grams of boric acid and 380.0 grams sodium hydroxide in 550.0 milliliters of distilled water followed by 850.0 grams of tetrapropylammonium bromide. To this solution, 3,375 grams of Ludox HS-40 were added with vigorous stirring continuing for about 15 minutes after addition. The resulting curdy, gelatinous mixture was placed in a stirred, sealed crystallization vessel to crystallize for six days at 145° C. The resulting crystalline material was recovered by filtration, washed thoroughly with distilled water, and dried in a forced draft oven at 165° C. for 16 hours. The dried material was program calcined consisting for four hours from 200° F. (93° C.) to 1,000° F. (538° C.), four hours at 1,000° F. (538° C.), and at least four hours from 1,000° F. (538° C.) to 200° F. (93° C.).

One hundred grams of sieve were exchanged with 100 grams of ammonium acetate in one liter of distilled water at 95° C. for 1.5 hours. The sieve then was filtered, washed with approximately 200 milliliters of distilled water, and filter dried. This procedure was repeated to obtain a total of five ammonium acetate exchanges with the last exchange receiving a wash of about 500 milliliters of water. The washed sieve was dried at 165° C. for approximately 16 hours (overnight). The dried sieve was program calcined with a program consisting of (a) a linear temperature rise of less than or equal to 200° F. per hour from 200° F. to 900° F., (b) holding at 900° F. for 4 hours, and (c) decreasing the temperature at a maximum of 200° F. per hour from 900° F. to 200° F. per hour. The calcined sieve then was exchanged with a solution containing 1,500 milliliters of 5% Ni $(NO_3)_2.6H_2O$ in distilled water. After exchanging for 2 hours at 90° C., the sieve was filtered from the exchange solution, washed with approximately 300 milliliters of distilled water and dried overnight in the forced draft oven at 165° C. The dried and exchanged sieve was program calcined at 900° F. with the program calcination procedure described above. The catalyst was prepared by dispersing the above calcined and exchanged sieve in PHF-alumina which is initially an acetic acid stabilized alumina hydrosol containing about 8.7% $Al_2O_3$. To 109 grams of calcined and exchanged sieve were added 121 grams of distilled water to fill the sieve pores with water. The wet sieve was then added and thoroughly mixed with 672 grams of alumina hydrosol. The mixture was gelled (solidified) with the addition of a solution containing 40 milliliters of distilled water and 40 milliliters of concentrated ammonium hydroxide. The resulting solid was then dried overnight in a forced air oven at 165° C. The dried solid was program calcined at 900° F. with the program as described above. The calcined solid was crushed and sized to 30 to 50 mesh (U.S. Sieve Series) and recalcined with the above 900° F. program calcination.

Twenty grams of the prepared 30–50 mesh catalyst were diluted with 162 of alpha alumina and placed in a one-inch diameter 316 stainless steel tube reactor. A solution of isobutylene in methanol was pumped in an upward flow manner in the reactor over the catalyst under the conditions and with the results shown in Table II.

TABLE II

| | | | |
|---|---|---|---|
| Reactor Temperature (°C.) | 93.3 | 104.4 | 104.4 |
| Reactor Pressure (atmos.) | 28.2 | 28.2 | 28.2 |
| Methanol/Isobutylene (molar ratio) | 1.0 | 1.0 | 1.2 |
| WHSV of Solution $(hr^{-1})$ | 3.0 | 3.0 | 3.0 |
| Yield of methyl t-butyl ether (wt. %) | 72 | 75 | 86 |

What is claimed is:

1. A process to form an ether comprising contacting an alkene and an alcohol under conversion conditions with an AMS-1B crystalline borosilicate catalyst composition.

2. The process of claim 1 wherein the alkene contains two to about six carbon atoms, the alcohol contains one to about eight carbon atoms and the resulting ether contains about four to about ten carbon atoms.

3. The process of claim 1 wherein the alkene contains about three to about five carbon atoms, the alcohol contains one to about three carbon atoms and the resulting ether contains about four to about six carbon atoms.

4. The process of claim 1 wherein the ether formed contains five carbon atoms.

5. The process of claim 1 wherein the alcohol is methanol and the alkene is a butene.

6. The process of claim 5 wherein the butene is isobutylene.

7. The process of claim 1 wherein an ion or molecule of a Group IB, IIB, IIIB, IVB, VB, VIB, VIIB or VIII metal or a rare earth element is contained in the AMS-1B borosilicate catalyst composition as an additional catalytically active material.

8. The process of claim 7 wherein the additional catalytically active material is nickel ion.

9. The process of claim 1 wherein the alcohol and alkene are converted at about 40° to about 200° C., at a pressure of about 10 to about 100 atmospheres and at a weight hourly space velocity of aoout 0.1 to about 24 $hr^{-1}$.

10. The process of claim 1 wherein the alcohol and alkene are converted at about 50° to about 150° C., at a pressure of about 12 to about 75 atmospheres and at a weight hourly space velocity of about 0.5 to about 12 $hr^{-1}$.

11. The process of claim 3 wherein the alcohol and alkene are converted at about 60° to about 140° C., at a pressure of about 15 to about 60 atmospheres and at a weight hourly space velocity of about 1.0 to about 10 $hr^{-1}$.

12. The process of claim, 1 wherein the AMS-1B crystalline borosilicate composition is incorporated with an alumina, silica or silica-alumina matrix.

13. A process to form methyl-t-butyl ether comprising contacting isobutylene and methanol under conversion conditions with an AMS-1B crystalline borosilicate catalyst composition comprising an AMS-1B crystalline borosilicate molecular sieve incorporated in an alumina or silica-alumina matrix.

14. The process of claim 13 wherein the AMS-1B crystalline borosilicate molecular sieve is incorporated in an alumina matrix.

15. The process of claim 13 wherein the methanol and isobutylene are converted at about 40° to about 200° C., at a pressure of about 10 to about 100 atmospheres and at a weight hourly space velocity of about 0.1 to about 24 $hr^{-1}$.

16. The process of claim 13 wherein nickel ion has been placed on the AMS-1B crystalline borosilicate catalyst composition.

17. A process to form methyl-t-butyl ether comprising contacting isobutylene and methanol under conversion conditions with an AMS-1B crystalline borosilicate catalyst composition comprising an AMS-1B crystalline borosilicate molecular sieve incorporated in an alumina matrix on which has been placed nickel ion.

18. The process of claim 17 wherein the methanol and isobutylene are converted at about 40° to about 200° C., at a pressure of about 10 to about 100 atmospheres and at a weight hourly space velocity of about 0.1 to about 24 $hr^{-1}$.

19. The process of claim 17 wherein the alcohol and alkene are converted at about 50° to about 150° C., at a pressure of about 12 to about 75 atmospheres and at a weight hourly space velocity of about 0.5 to about 12 $hr^{-1}$.

20. The process claim 17 wherein the alcohol and alkene are converted at about 60° to about 140° C., at a pressure of about 15 to about 60 atmospheres and at a weight hourly space velocity of about 1.0 to about 10 $hr^{-1}$.

* * * * *